(12) United States Patent
Charles (10) Patent No.: US 8,080,029 B2
(45) Date of Patent: Dec. 20, 2011

(54) SYSTEM FOR ACTUATION OF A VITREOUS CUTTER

(75) Inventor: Steven T. Charles, Memphis, TN (US)

(73) Assignee: Novartis AG, Basel (CH)

( * ) Notice: Subject to any disclaimer, the term of this patent is extended or adjusted under 35 U.S.C. 154(b) by 334 days.

(21) Appl. No.: 11/859,270

(22) Filed: Sep. 21, 2007

(65) Prior Publication Data

US 2009/0082715 A1    Mar. 26, 2009

(51) Int. Cl.
*A61B 17/32* (2006.01)
(52) U.S. Cl. ................................ 606/169; 173/206
(58) Field of Classification Search .................. 606/169, 606/171, 170, 177, 178; 604/22, 67, 131–134, 604/139–141, 153; 91/232, 234, 325; 433/118; 600/562–570; 173/168, 206
See application file for complete search history.

(56) References Cited

U.S. PATENT DOCUMENTS

| | | | |
|---|---|---|---|
| 812,163 A | 2/1906 | Bernis | |
| 2,016,746 A | 10/1935 | Ireland | |
| 2,707,389 A | 5/1955 | Fortier | |
| 3,084,674 A | 4/1963 | Watson | |
| 3,477,665 A | 11/1969 | Legrand | |
| 3,646,727 A | 3/1972 | Wachsmuth | |
| 3,703,139 A | 11/1972 | Furlong | |
| 3,704,651 A * | 12/1972 | Kupka | 91/232 |
| 3,740,960 A * | 6/1973 | Erma | 60/542 |
| 3,854,382 A | 12/1974 | Walters et al. | |
| 3,867,934 A | 2/1975 | Ollivier | |
| 3,896,701 A * | 7/1975 | Crewse | 91/7 |
| 4,014,342 A | 3/1977 | Staub et al. | |
| 4,077,567 A | 3/1978 | Ginn et al. | |
| 4,086,804 A | 5/1978 | Ruby | |
| 4,164,167 A | 8/1979 | Imai et al. | |
| 4,253,480 A | 3/1981 | Kessel et al. | |
| 4,323,064 A | 4/1982 | Hoenig et al. | |
| 4,331,130 A | 5/1982 | Lewicky | |
| 4,344,144 A | 8/1982 | Damico et al. | |
| 4,476,532 A | 10/1984 | Akiyama et al. | |
| 4,590,935 A | 5/1986 | Ranalli | |
| 4,622,503 A | 11/1986 | Sundblom et al. | |
| 4,650,460 A | 3/1987 | Roizenblatt | |
| 4,650,462 A | 3/1987 | DeSatnick et al. | |
| 4,679,583 A | 7/1987 | Lucas et al. | |
| 4,706,687 A | 11/1987 | Rogers et al. | |
| 4,757,814 A | 7/1988 | Wang et al. | |
| 4,770,654 A | 9/1988 | Rogers et al. | |

(Continued)

FOREIGN PATENT DOCUMENTS

DE    39 25 405 A1    2/1991

(Continued)

OTHER PUBLICATIONS

Abstract of Kabei, Shimemura, et al., A portable pneumatic driving unit for a left ventricular assist device, Int. J. Artif. Organs, 1988, 186-90, 11(3).

(Continued)

*Primary Examiner* — S. Thomas Hughes
*Assistant Examiner* — Katherine M Shi (57) ABSTRACT

Embodiments of systems and methods disclosed herein regard simplifying and improving the performance and reliability of pneumatic actuators operable to actuate surgical cutters or shears. Various embodiments include systems and methods for vitreous cutting apparatuses utilizing self-valving vitreous cutters that actuate at a frequency based on the properties of the vitreous cutter.

19 Claims, 9 Drawing Sheets

U.S. PATENT DOCUMENTS

| | | | |
|---|---|---|---|
| 4,790,816 A | 12/1988 | Sundblom et al. | |
| 4,810,242 A | 3/1989 | Sundblom et al. | |
| 4,840,111 A | 6/1989 | Garnjost | |
| 4,933,843 A | 6/1990 | Scheller et al. | |
| 5,020,315 A | 6/1991 | Leachman, Jr. et al. | |
| 5,020,825 A | 6/1991 | Lizell | |
| 5,092,178 A | 3/1992 | Vanderlaan | |
| 5,094,260 A | 3/1992 | Stuart et al. | |
| 5,154,207 A | 10/1992 | Bolt | |
| 5,176,628 A | 1/1993 | Charles et al. | |
| 5,237,309 A * | 8/1993 | Frantz et al. | 340/679 |
| 5,239,861 A | 8/1993 | Fujita et al. | |
| 5,314,295 A | 5/1994 | Lukkari et al. | |
| 5,417,246 A | 5/1995 | Perkins et al. | |
| 5,474,532 A | 12/1995 | Steppe | |
| 5,549,139 A | 8/1996 | Perkins et al. | |
| 5,571,248 A | 11/1996 | Seetharaman et al. | |
| 5,580,347 A | 12/1996 | Reimels | |
| 5,587,536 A | 12/1996 | Rasmussen | |
| 5,669,923 A * | 9/1997 | Gordon | 606/170 |
| 5,674,194 A | 10/1997 | Jung et al. | |
| 5,829,335 A | 11/1998 | Ewald et al. | |
| 5,846,257 A | 12/1998 | Hood | |
| 5,857,485 A | 1/1999 | Perkins et al. | |
| 5,979,494 A | 11/1999 | Perkins et al. | |
| 6,155,233 A | 12/2000 | Wade et al. | |
| 6,162,187 A | 12/2000 | Buzzard et al. | |
| 6,383,203 B1 * | 5/2002 | Makihara | 606/171 |
| 6,450,966 B1 | 9/2002 | Hanna | |
| 6,561,143 B2 * | 5/2003 | Holtzman | 123/73 V |
| 6,575,990 B1 | 6/2003 | Wang et al. | |
| 7,244,240 B2 | 7/2007 | Nazarifar et al. | |
| 7,335,217 B2 | 2/2008 | Wang et al. | |
| 7,470,277 B2 | 12/2008 | Finlay et al. | |
| 7,775,052 B2 | 8/2010 | Cornwell et al. | |
| 2003/0042182 A1 | 3/2003 | Moscaritolo | |
| 2003/0208305 A1 | 11/2003 | Junk et al. | |
| 2004/0154466 A1 | 8/2004 | Gethmann et al. | |
| 2006/0271082 A1 | 11/2006 | Kirchhevel et al. | |
| 2007/0185512 A1 | 8/2007 | Kirchhevel | |
| 2007/0270735 A1 | 11/2007 | Williams et al. | |
| 2007/0270746 A1 | 11/2007 | King | |
| 2007/0282262 A1 | 12/2007 | Williams et al. | |
| 2008/0082077 A1 | 4/2008 | Williams | |
| 2008/0142093 A1 | 6/2008 | Turner et al. | |
| 2008/0146988 A1 | 6/2008 | Olivera et al. | |
| 2008/0149197 A1 | 6/2008 | Turner et al. | |
| 2008/0168985 A1 | 7/2008 | Turner et al. | |
| 2009/0030436 A1 | 1/2009 | Charles | |
| 2009/0124962 A1 | 5/2009 | Hopkins et al. | |
| 2009/0203480 A1 | 8/2009 | Petzold et al. | |
| 2009/0259242 A1 | 10/2009 | Gerg et al. | |
| 2010/0145374 A1 | 6/2010 | Perkins et al. | |

FOREIGN PATENT DOCUMENTS

| | | |
|---|---|---|
| DE | 42 32 586 A1 | 3/1994 |
| DE | 198 21 420 C1 | 10/1999 |
| DE | 10247869 A1 | 5/2004 |
| DE | 20 2005 009670 U1 | 9/2005 |
| DE | 10247869 B4 | 2/2007 |
| EP | 0469641 B1 | 6/1989 |
| EP | 0626628 A1 | 11/1994 |
| EP | 0673475 B1 | 6/1996 |
| EP | 0626628 B1 | 12/1997 |
| EP | 0 884 667 A1 | 6/1998 |
| EP | 874163 A2 | 10/1998 |
| EP | 1074271 A2 | 2/2001 |
| EP | 1 172 586 A1 | 1/2002 |
| EP | 1074271 A3 | 2/2002 |
| EP | 1074271 B1 | 10/2004 |
| EP | 1660244 B1 | 12/2006 |
| EP | 2032878 B1 | 12/2009 |
| GB | 792397 A | 3/1958 |
| GB | 1 213 723 A | 11/1970 |
| GB | 1 323 788 A | 7/1973 |
| GB | 2 016 746 A | 9/1979 |
| GB | 2 140 871 A | 12/1984 |
| GB | 2 389 423 A | 12/2003 |
| JP | 7259801 | 10/1995 |
| JP | 9225698 | 9/1997 |
| JP | 9311091 A | 12/1997 |
| WO | WO 95/31141 A1 | 11/1995 |
| WO | WO 00/78371 A1 | 12/2000 |
| WO | WO 01/64120 A1 | 9/2001 |
| WO | WO 2008/000599 A1 | 1/2008 |
| WO | WO 2008/054944 A1 | 5/2008 |
| WO | WO 2008/105950 A2 | 9/2008 |
| WO | WO 2008/105950 A3 | 9/2008 |
| WO | WO 2008/140537 A1 | 11/2008 |
| WO | WO 2008/147429 A2 | 12/2008 |
| WO | WO 2008/147429 A3 | 12/2008 |
| WO | WO2008147429 | 12/2008 |
| WO | WO 2010/066302 A1 | 6/2010 |

OTHER PUBLICATIONS

Abstract of Nachlas, Marvin, et al., A simple portable pneumatic pump for external cardiac massage, The American Journal of Cardiology, 1962, 107-109, 10(1).

Abstract of J.L. Waldeck; "The Development of a Portable Pressure Source for the Static and Dynamic Calibration of Pressure Transducers"; Journal of Wind Engineering and Industrial Aerodynamics, 1987, 213-230, 26(2).

Abstract of Ellis, George, et al., Microcomputer-Controlled Precision Pressure Generator, IEEE Transactions on Instrumentation and Measurement, 1977, 214-217, 26(3).

Abstract of Whalen, R.L., et al., An electromagnetic pneumatic blood pump driver, American Society of Artificial Internal Organs, 1988, 721-725, 34(3).

Abstract of Turkentine, R.B., et al., Pressure-operated shutter for thin-film monitor, Journal of Physics E: Scientific Instruments, 1979, 12(1).

Abstract of Rogers, Richard C., An inexpensive picoliter-volume pressure ejection system, Brain Research Bulletin, 1985, 669-671, 15(6).

Abstract of Johnson, Kenneth S., et al., A submersible flow analysis System, Analytical Chimica Acta, 1986, 245-257, 179.

Abstract of Tabassum, Alim Abid, Solar refrigeration: evaluation of technical options and design of a solar-generator-adsorber for a novel adsorption refrigerator, Cranfield Univ., 1989.

Abstract of Buchanan, P.R., et al., Recovery of ventilation distributions by gas wash-out of a mechanical pump, Clinical Physics and Physiological Measurement, 1986, 7(3).

International Searching Authority, International Report on Patentability, PCT/US2007/079915, May 5, 2009, 6 pages.

International Searching Authority, International Report on Patentability, PCT/US2007/080265, Sep. 1, 2009, 8 pages.

International Searching Authority, International Report on Patentability, PCT/US2007/080540, Jun. 23, 2009, 5 pages.

International Searching Authority, International Report on Patentability, PCT/US2007/080239, Jun. 16, 2009, 8 pages.

* cited by examiner

SYSTEM FOR ACTUATION OF A VITREOUS CUTTER

TECHNICAL FIELD OF THE INVENTION

This disclosure relates to surgical systems. More particularly, embodiments of systems and methods described herein relate to surgical instrumentation used for removing vitreous fluid and tissues from the eye during ophthalmic surgery. Even more particularly, embodiments of systems and methods described herein regard actuating surgical instruments used for removing vitreous fluid and tissues from the eye.

BACKGROUND OF THE INVENTION

The posterior segment (i.e. behind the natural lens) of the eye is filled with a jellylike substance called the vitreous. It may be necessary to remove damaged vitreous as part of eye surgery. An eye surgery operation performed to remove vitreous is called vitreous surgery (vitrectomy). When the vitreous is removed, the body quickly replaces it with a substitute clear liquid.

A surgical instrument used in vitreous surgery typically is a hand-held vitreous cutter comprising a probe that is inserted into the eye through an incision and includes a tube which draws in a portion of vitreous. The probe also includes a cutting mechanism which severs vitreous, allowing vitreous to be drawn out through the tube by suction.

The probe generally consists of a concentric arrangement of an inner tube driven by an actuator in an outer tube, with the outer tube extending distally beyond the inner tube. The outer tube has an opening at or near its distal tip. When suction is applied to the inner tube, a portion of vitreous is pulled into the opening of the outer tube. When the inner tube is then driven axially forward by the actuator, it shears off the vitreous portion projecting through the opening in the outer tube. The vitreous material is then aspirated through the inner tube by a suction source.

SUMMARY OF THE INVENTION

This disclosure describes systems and methods for a pneumatic actuator of a vitreous cutter which may be simpler, more reliable and cheaper to produce than prior art systems and methods for actuators operable to actuate vitreous cutters. One embodiment of systems disclosed herein includes a pneumatic actuator operable to actuate at a resonant frequency based on one or more components of the actuator. One embodiment of a vitreous cutting apparatus can comprise an actuator body defining an input port and an exhaust port, an actuating member movable in the actuator body from a first position to a second position, a diaphragm coupled to the actuator body and the actuating member to form a chamber accessed by the input port and the exhaust port and a tube coupled to the actuating member. The actuating member is movable from the first position in which the input port is open to the chamber and the exhaust port is blocked and to the second position in which the exhaust port is open to the chamber and the input port blocked. The vitreous cutting apparatus can further include a passive valve located upstream of the input port having a threshold opening pressure. In one embodiment, the passive valve may be a reed or pop-off valve. The mechanical resonance frequency of the valve mechanism would determine the cutting rate.

Another embodiment of a vitreous cutter can comprise an actuator body defining an first input port, a second input port, a first exhaust port and a second exhaust port, an actuating member movable in the actuator body from a first position to a second position, a diaphragm coupled to the actuator body and the actuating member to form a first chamber accessed by the first input port and the first exhaust port and a second chamber on the obverse side of the diaphragm accessed by the second input port and the second exhaust port and a tube coupled to the actuating member. The actuating member is movable from the first position in which the first input port is open to the first chamber, the first exhaust port is blocked, the second exhaust port is open to the second chamber and the second input port is blocked to the second position in which the first exhaust port is open to the first chamber and the first input port blocked, the second input port is open to the second chamber and the second exhaust port is blocked.

This disclosure enables methods comprising utilizing a vitreous cutter in the context of vitreous surgery. For example, the distal end of a probe comprising a cutting mechanism may be inserted into an eye and the cutting mechanism actuated by an embodiment of a pneumatic actuator described in this disclosure such that the cutting mechanism cuts or severs vitreous and collagen fibers within the vitreous.

Embodiments of a pneumatic actuator may actuate at a resonant frequency of the actuator or one or two input valves. The resonant frequency may be a high frequency such that the actuator causes a vitreous cutter to perform cuts at high cutting rates, allowing for non-pulsatile cutting of vitreous and limiting the effects of cutting on the surrounding vitreous and other eye tissue. High cutting rates reduce the possibility of uncut vitreous collagen fibers passing through the port.

BRIEF DESCRIPTION OF THE FIGURES

A more complete understanding of systems and methods disclosed herein and the advantages thereof may be acquired by referring to the following description, taken in conjunction with the accompanying drawings in which like reference numbers indicate like features and wherein.

DETAILED DESCRIPTION

Embodiments of systems and methods disclosed herein are illustrated in the FIGURES, like numerals being used to refer to like and corresponding parts of the various drawings.

Figure 1:
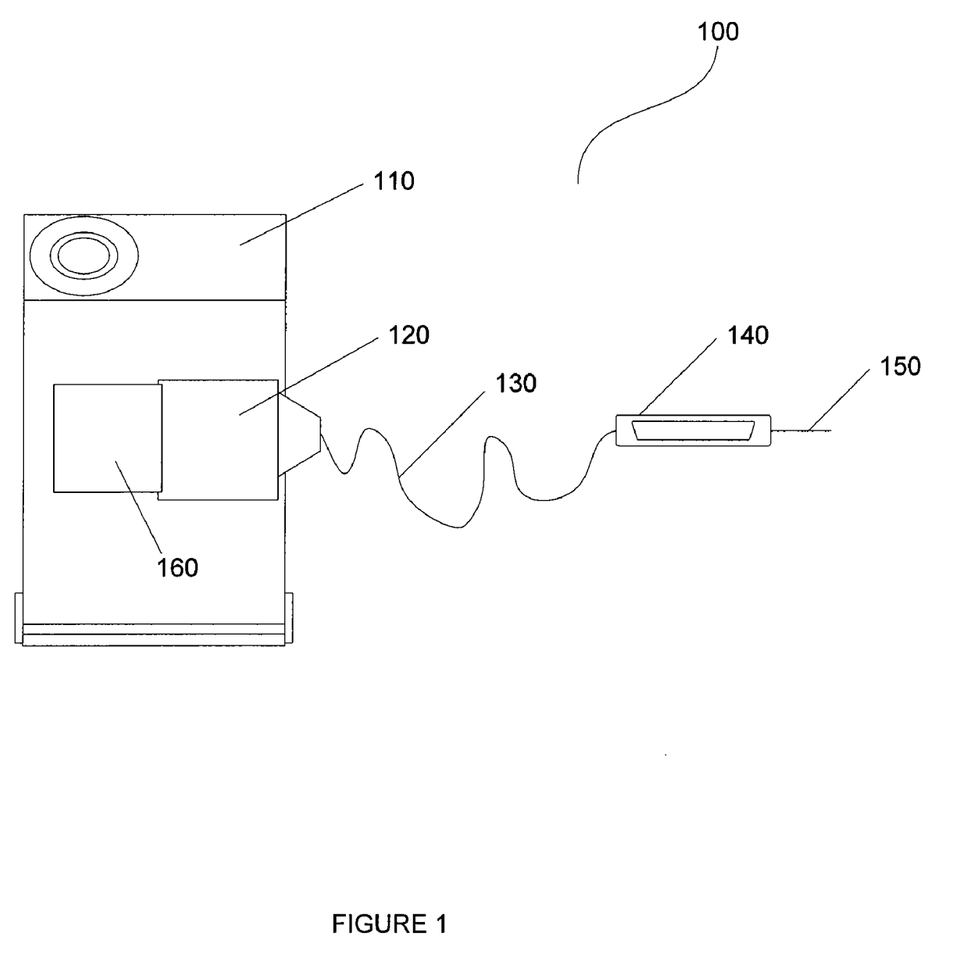
FIG. 1 is a diagrammatic representation of an embodiment of a surgical system operable to perform vitreous surgery.

FIG. 1 is a diagrammatic representation of one embodiment of a surgical system 100 which can be used to perform vitrectomy. Surgical system 100 includes a surgical machine 110, e.g. a vitrectomy machine, containing a pneumatic energy source 120 such as a compressor, gas tank with pressure regulator, or gas connection to external source with regulator capable of generating pneumatic pressure. Pneumatic energy source 120 is coupled to vitreous cutter apparatus 140 through tube 130 such that air or other fluid compressed by pneumatic energy source 120 is provided to vitreous cutter 140 to actuate a cutter integral to probe 150. When probe 150 is inserted into an eye, the cutter integral to probe 150 may cut vitreous. Surgical machine 110 may further include vacuum generator 160 which may be coupled to vitreous cutter 140 through tube 130 such that a suction may be generated which pulls cut vitreous into vitreous cutter 140 such that cut vitreous or other tissue is removed from the eye.

A popular type of vitreous cutter is the guillotine or axial vitreous cutter having a probe comprising a concentric arrangement of an inner tube and an outer tube. The outer tube has an opening adjacent to its distal tip which is inserted into the eye for surgery. When suction is applied to the probe, vitreous is pulled into the opening of the outer tube. The inner tube is then pushed axially forward by an actuator and shears off the vitreous material pulled through the opening in the outer tube. The vitreous material is then aspirated through the inner tube by an external suction source. This process is cyclically repeated, allowing for the removal of vitreous or other tissue.

Figures 2A, 2B:
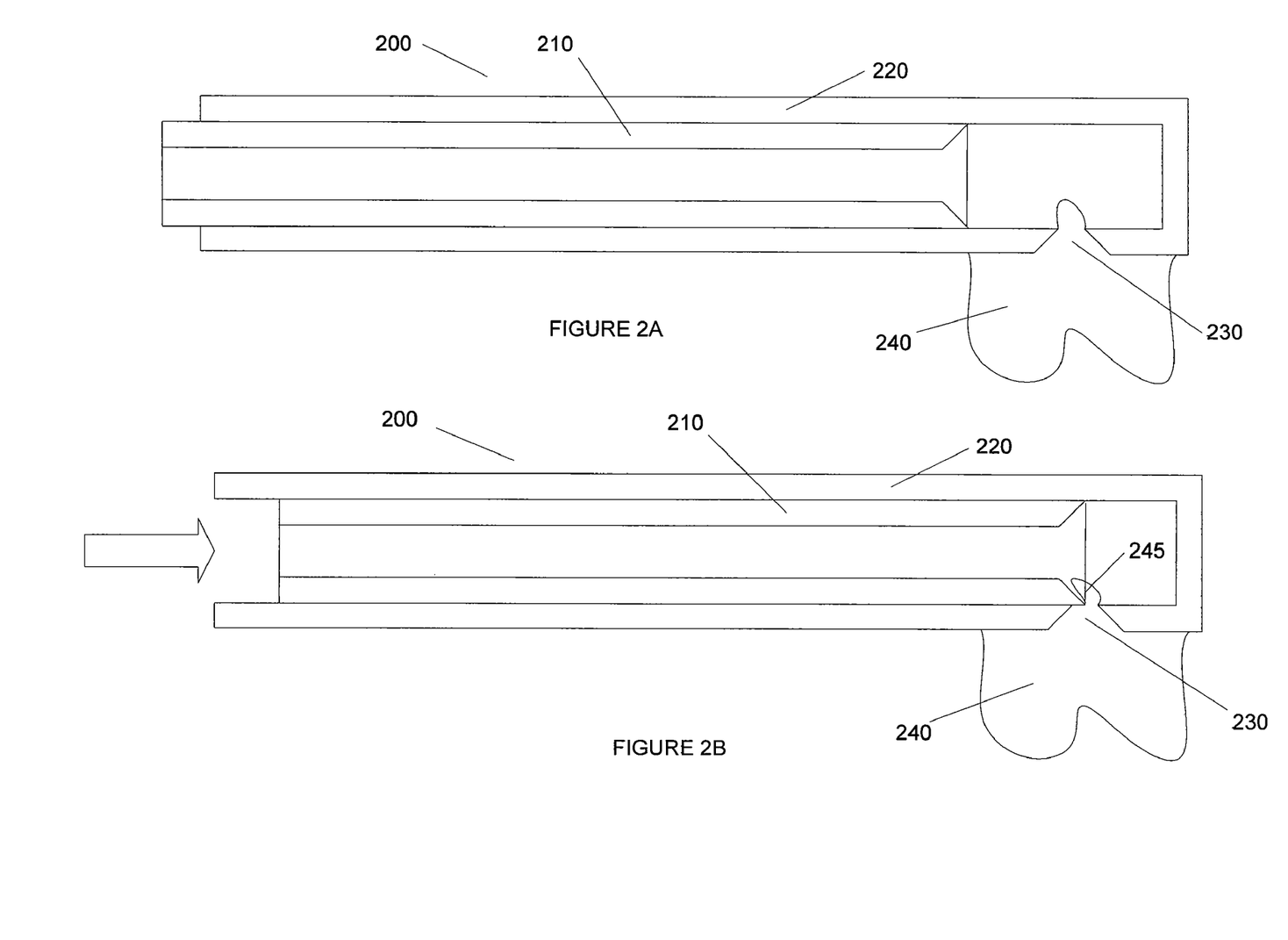
FIGS. 2A-2D are diagrammatic representations of one embodiment of a portion of a probe comprising one embodiment of a vitreous cutter.

FIGS. 2A-2D are diagrammatic representations of a portion of an axial vitreous cutter. FIG. 2A is a diagrammatic representation of a portion 200 of a probe (e.g. probe 150 of FIG. 1) operable to cut vitreous. Probe portion 200 comprises concentric tubes: inner tube 210 and outer tube 220. Inner tube 210 may be actuated such that it moves laterally within outer tube 220. Outer tube 220 is punctuated by an opening 230 at or near the distal end which is inserted into the eye. During a procedure, probe portion 200 is inserted into an eye such that opening 230 is surrounded by vitreous 240. A vacuum or other suction pulls jelly-like vitreous 240 into probe portion 200a through opening 230.

In FIG. 2B, inner tube 210 is pushed laterally towards the distal end of probe portion 200 such that the distal portion of inner tube 210 (which may be sharpened) begins to cut vitreous portion 245 protruding into probe portion 200b through opening 230.

Figure 2C:
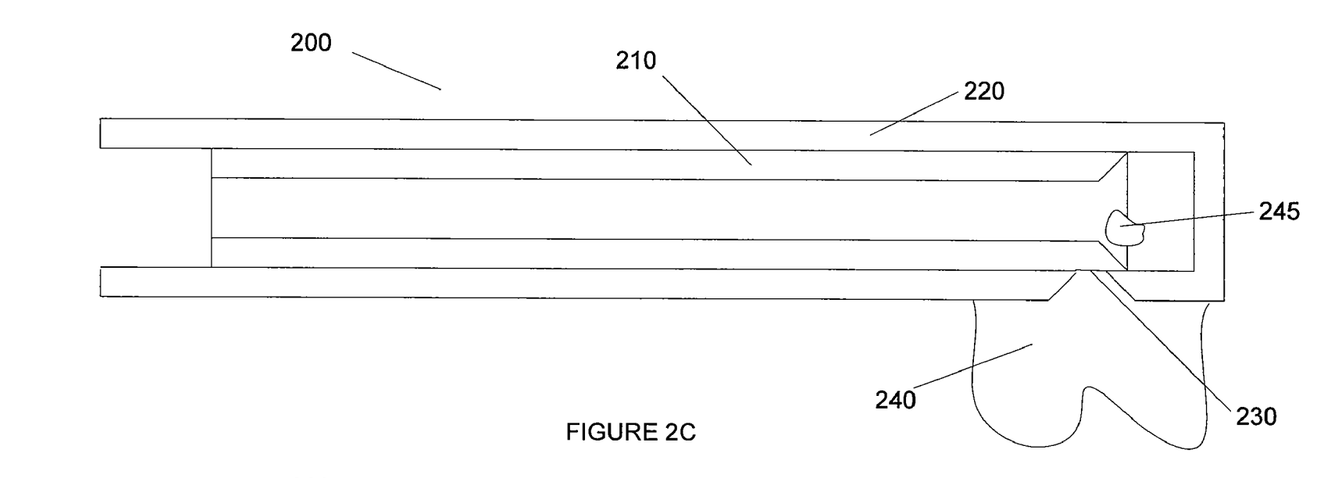
Figure 2D:
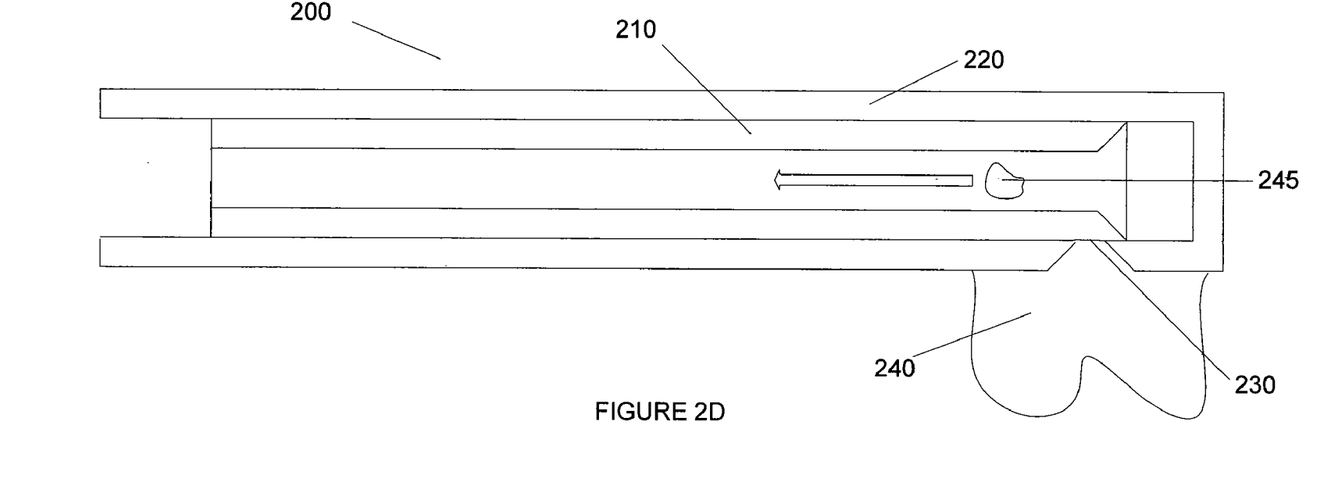

In FIG. 2C portion 200 is illustrated with distal end of inner tube 210 pushed past opening 230 in outer tube 220, severing vitreous portion 245. In FIG. 2D portion 200 is illustrated with inner tube 210 pushed past opening 230 in outer tube 220 to close opening 230. The force of the vacuum or other suction pulls vitreous portion 245 through the hollow of inner tube 210 and out of the eye cavity. In various embodiments of vitreous surgical systems, cut vitreous may be collected at the vitreous cutter apparatus, at a surgical machine or vented to a collection apparatus. The process depicted in FIGS. 2A-2D may be cyclically repeated to remove vitreous or other tissue.

In another embodiment of a vitreous cutter, instead of axial motion being used to sever vitreous, rotational action can be used to sever vitreous. Vitreous cutters relying on rotational action to sever vitreous are referred to as rotary or rotational action vitreous cutters. In one embodiment, translational movement of an actuator can be converted into rotational cutting movement to produce a rotary action vitreous cutter.

Figure 3:
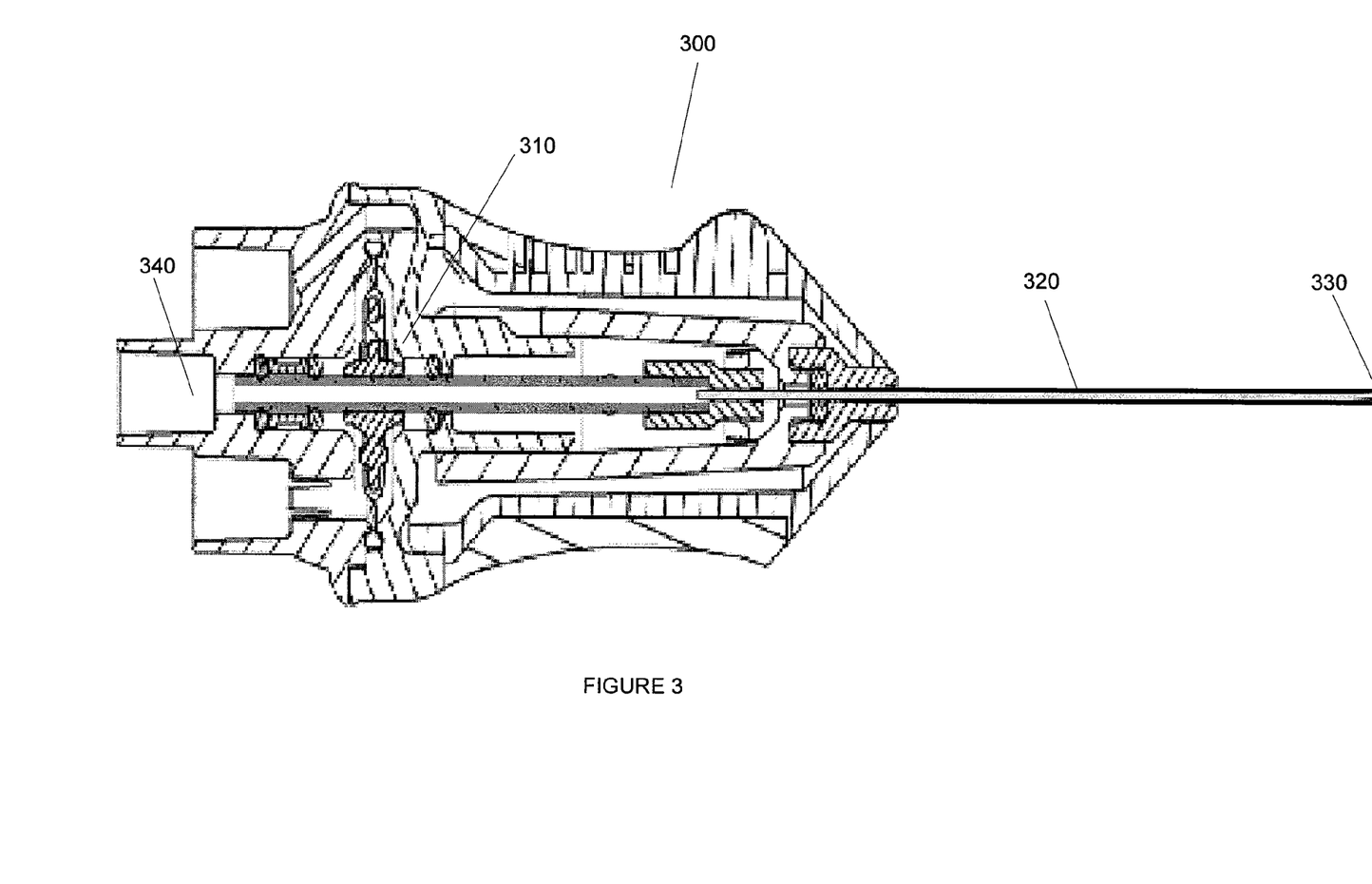
FIG. 3 is a diagrammatic representation of one embodiment of a vitreous cutter.

FIG. 3 is a diagrammatic representation of a vitreous cutter 300. Vitreous cutter 300 may be a handheld vitreous cutter comprising an actuator 310 which actuates the inner tube of a probe 320, causing the operation of a cutter 330 located at the distal end of probe 320 which is inserted into the eye. Vitreous cutter may further comprise a suction port 340. Suction port 340 may be coupled to a vacuum generator located, for example, at a surgical machine, e.g. surgical machine 110 of FIG. 1. Suction port 340 may further be coupled to probe 320 such that vitreous cut by the cutter at the distal end of probe 320 may be suctioned out of probe 320 out suction port 340. The vacuum generator may be operated to generate a vacuum providing suction which pulls cut vitreous out of probe 320 and out of vitreous cutter 300 through suction port 340.

A pneumatic actuator powered by a pneumatic power source such as a compressor or gas tank may be utilized to actuate the inner tube of a probe or other element of a vitreous cutter. In the context of an axial vitreous cutter, actuation of the inner tube causes translational movement of the inner tube, resulting in the cutting of vitreous as shown above in FIGS. 2A-2D. A pneumatic actuator may comprise one or more valves which control or channel pneumatic power (e.g. pressure) and a resilient diaphragm driven by channeled pneumatic pressure and coupled to the inner tube of a probe such that movement of the diaphragm actuates the inner tube, causing translational movement of the inner tube. In one embodiment, a pair of valves may be used in conjunction with a pneumatic power source and a diaphragm to form a pneumatic actuator operable to actuate the inner tube of an axial cutter.

In previous pneumatic vitreous cutters, the inner tube was typically actuated by the use of valves in a surgical machine (e.g. surgical machine 110 of FIG. 1). Pressure was alternatively provided to each side of the diaphragm in timed pulses. In order to provide appropriately timed pulses, appropriate valves had to be chosen and a valve control algorithm developed to generate valve control signals to sequence the valves. It was a difficult and time-consuming process to select the correct valves and valve timings to achieve the proper actuator motion. Development of the correct valve control sequence was a non-trivial task as it has to account for the different rise times and settling times of the valves and other factors in controlling multiple valves. Furthermore, sending pulsed air through a tube to the vitreous cutter could cause the tubing or cutter to vibrate during a procedure. Embodiments described herein address these shortcomings by providing a self-resonating actuator that actuates at a frequency based on applied pressures and the mechanical characteristics of the cutter.

FIGS. 4A-4D illustrate an embodiment of a portion of a vitreous cutter 400. Vitreous cutter 400 includes an actuator body 420 that, according to one embodiment, can form a generally cylindrical cavity 410. Vitreous cutter 400 can further comprise an actuating member 430 that is movable in actuator body 420 and is coupled to an inner tube 440 of vitreous cutter 400 (i.e., the reciprocating inner tube of the vitreous cutter's probe). Actuating member 430 can be generally disk shaped with an annularly disposed gap 435, but may have other suitable shapes. Actuating member 430 can be further coupled to a diaphragm 450. Diaphragm 450 can be a sheet of a resilient material such as Mylar, a resilient composite or other material. Actuator body 420, actuating member 430 and diaphragm 450 can form a chamber 460 that can be pressurized. Although shown as single pieces, each of actuating body 420, actuating member 430 and diaphragm 450 can comprise multiple pieces.

Actuator body 420 can define one or more ports for the inlet and outlet of fluid. For example, actuator body 420 can define input port 474 and exhaust port 478. Input port 474 can be coupled to a pneumatic power coupling 480 by a fluid flow passage 482. Exhaust port 478 can be coupled to an exhaust chamber, a vacuum, atmosphere or other area to which fluid can be exhausted from chamber 460. In one embodiment, a pneumatic power source (e.g., a compressor) contained in a surgical machine is coupled to pneumatic power coupling 480 through tubing, allowing the actuator to be remote from a pneumatic power source and contained in a handheld vitreous cutting apparatus. A passive valve 490, that is a valve that does not require active control such as a reed valve, pop-off valve or other valve that opens at a threshold pressure and closes below the threshold pressure, may be disposed in inlet flow passage 482 or other position between pneumatic energy source 480 and input port 474.

In operation, fluid (e.g., air or other fluid) can be pressurized in inlet flow passage 482. When the fluid reaches the threshold pressure of valve 490, valve 490 opens and fluid flows through input port 474, through gap 435 into chamber 460, thereby increasing the pressure in chamber 460. This will cause diaphragm 450 to distend and actuating member 430 to move forward. As diaphragm 450 distends, it will assert an increasing force on actuating member 430 in the opposite direction to the movement of actuating member 430. As actuating member 430 moves forward, actuating member 430 partially or fully blocks input port 474, preferably sealing input port 474. Furthermore, as actuating member 430 moves forward, gap 435 becomes aligned with exhaust port 478 to expose exhaust port 478 to chamber 460. With input port 474 closed and exhaust port 478 open, the pressure in chamber 460 will drop as the pressurized fluid is exhausted. The force on actuating member 430 by diaphragm 450 will force actuating member 430 back to its original position.

Diaphragm 450 acts similarly to a spring under dynamic cyclical loading created by the introduction and exhaustion of pressurized fluid in chamber 460. Consequently, actuating member 430 will actuate with a frequency based on the mechanical properties of diaphragm 450 (i.e., the "spring-like" characteristics) and the force cyclically applied by the pressure in chamber 460. For a given maximum pressure of fluid in chamber 460 (as determined by the input pressure in inlet flow passage 482) and diaphragm 450, actuating member 430 will move back and forth at the resonance frequency of the system.

Figure 4A:
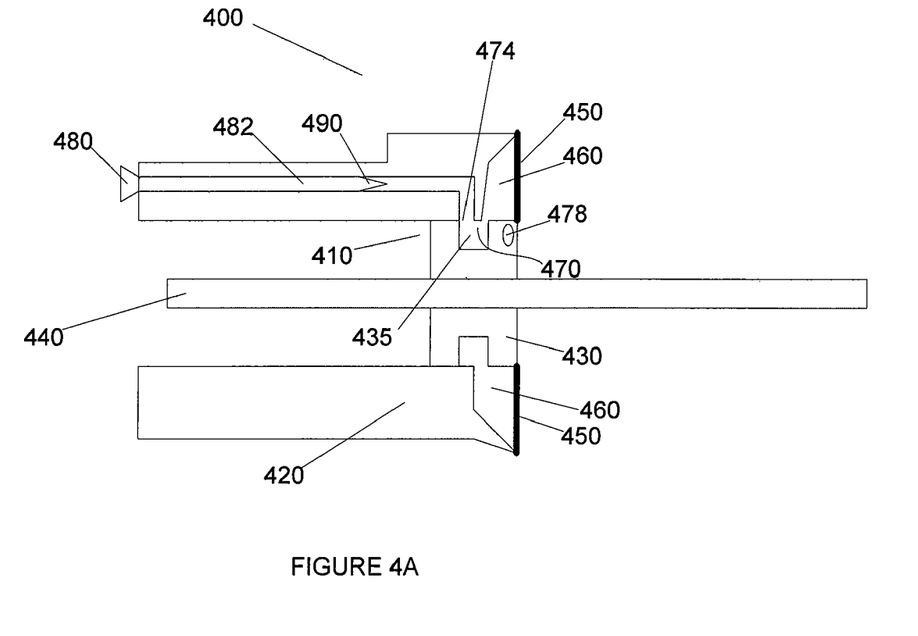
FIGS. 4A-4D are diagrammatic representations of a portion of one embodiment of a vitreous cutter.

In FIG. 4A, chamber 460 may be isolated from a pneumatic power source by passive valve 490 in the inlet flow path 482 of input port 474. A pneumatic power source may be operated such that pneumatic power in the form of pressurized air or other fluid enters flow passage 482 through pneumatic power coupling 480 but is prevented from entering chamber 460 by passive valve 490. In a non-cutting state, pneumatic power may be applied to input port 474 such that the pressure in input port 474 is below the pressure necessary to open the reed valve. This state can correspond to a time in which a surgeon is not cutting with the vitreous cutter. Preferably, the pressurized fluid is provided at a pressure that is just below the pressure necessary to open passive valve 490. For example, if valve 490 opens at 30 psi (gauge), pressurized fluid at 10 psi to 29 psi (gauge) can be provided so that a portion of passage 482 is charged, but passive valve 490 does not open. In various embodiments, valve 490 may have different opening thresholds. One advantage of applying a pressure that is near the threshold for opening valve 490 is that only a small increase in pressure is required to begin cutting. This decreases the magnitude of pressure pulses in pneumatic tubing and at the cutter 400.

Figure 4B:
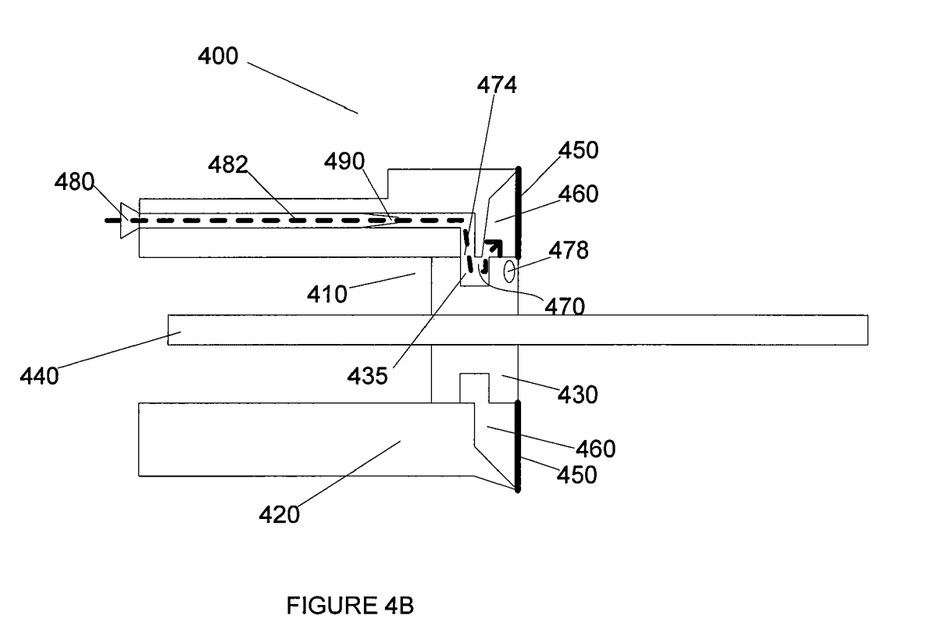

In FIG. 4B, the pneumatic power source passive is operated such that the pressure in the input port upstream of passive valve 490 is raised above the opening threshold of passive valve 490 causing passive valve 490 to open thereby allowing pressurized air or other fluid to enter chamber 460 through input port 474 (denoted in FIG. 4B by the bold dashed directional line). The pressurized air or other fluid fills chamber 460, causing displacement of diaphragm 450, which in turn causes translational movement of actuating member 430 and inner tube 440. Preferably, the pressure applied is slightly greater than opening pressure of passive valve 490. Again, using the example of a reed valve with a threshold pressure of 30 psi (gauge), 31-40 psi (gauge) can be applied.

Figure 4C:
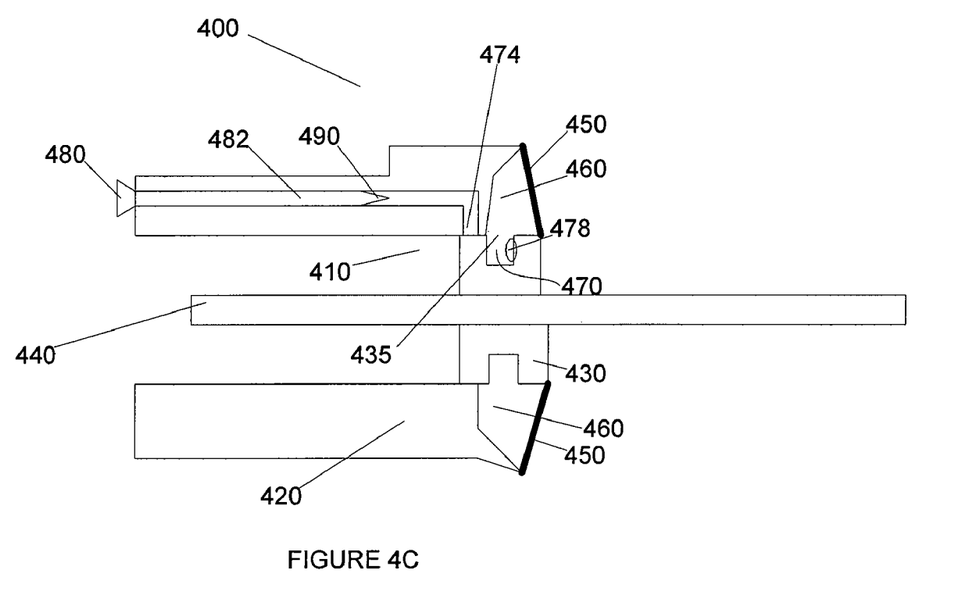

As shown in FIG. 4C, the pressurized air or other fluid which entered chamber 460 has displaced diaphragm 450, causing translational movement of actuating member 430 and inner tube 440. The translational movement of actuating member 430 has caused a portion of actuating member 430 of block input port 474 such that pressurized air or other fluid is prevented from entering chamber 460 through input port 474. The translational movement of actuating member 430 has displaced the portion of actuating member 430 previously blocking exhaust port 478 such that exhaust port 478 is coupled to chamber 460 by gap 435. Exhaust port 478 may be coupled to an area of lower pressure than chamber 460, thus the pressurized air or other fluid vents out exhaust port 478. In one embodiment, exhaust port 478 vents to atmosphere such that the pressure in chamber 460 returns to atmosphere when exhaust port 478 is open to chamber 460.

Figure 4D:
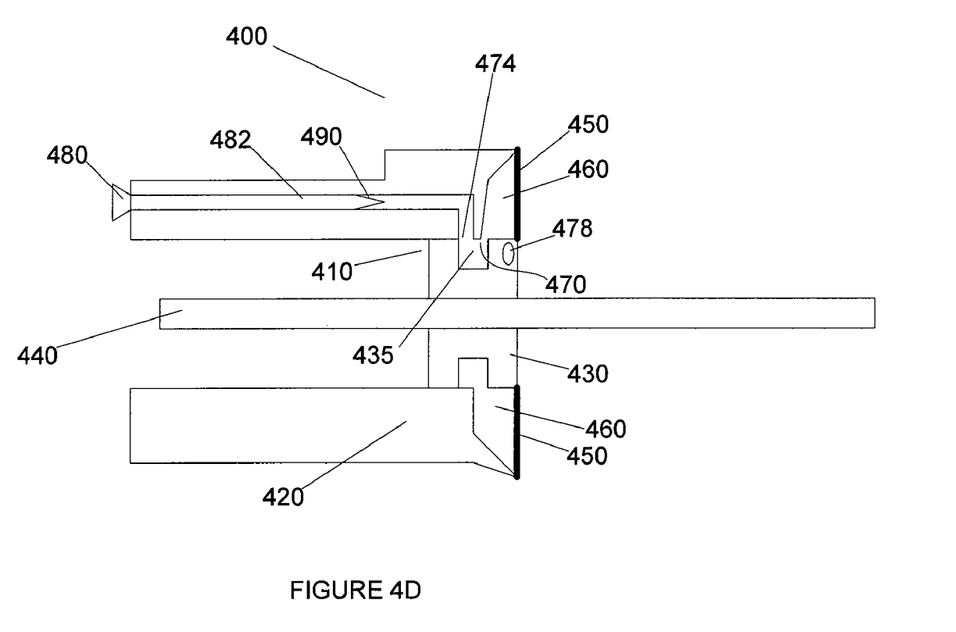

Because, as described with regard to FIG. 4C, the pressure in chamber 460 is vented out exhaust port 478, the elasticity of diaphragm 450 returns diaphragm 450 to approximately its original position causing the translational movement of actuating member 430 to approximately its position as depicted in FIG. 4A. The movement of actuating member 430, in turn, causes the translational movement of attached inner tube 440 to approximately its position as depicted in FIG. 4A. FIG. 4D depicts the portion of vitreous cutter 400 at a time at which the elasticity of diaphragm 450 has returned diaphragm 450, actuating member 430 and inner tube 440 to their positions in FIG. 4A. If the pressure in input port 474 upstream of passive valve 490 is still above the opening threshold of passive valve 490 the process of FIGS. 4B-4D will repeat. Thus, the above described processes causing the translational movement of inner tube 440 may be cyclically repeated so long as the air pressure applied to vitreous cutter 400 is above the opening threshold of passive valve 490, thus actuating inner tube 440.

The portion of vitreous cutter 400 as depicted in FIGS. 4A-4D is merely one embodiment for actuating a vitreous cutter that can be constructed utilizing a passive valve conjunction with a spindle or slide valve. Thus, the embodiments of FIGS. 4A-4D are provided by way of example and not limitation: any number of other actuators as would be understood by one or skill in the art may be constructed utilizing a passive valve or similar pressure activated valve in conjunction with a spindle or similar valve. For example, a spring or other device may be coupled to actuating member 430 or inner tube 440 to ensure that the rest position is such that input port 474 is open. Additionally, instead of being used to activate an axial cutter, a variant of the above described actuator may be coupled to an apparatus which converts translational movement into rotational cutting action to allow the above described actuator to actuate a rotary action vitreous cutter.

Embodiments of the above described actuator may be resonant and self-valving. That is, a steady pressure may be applied to a vitreous cutting apparatus which results in a vitreous cutter being actuated at a frequency determined in part by the resonance of the system. Accordingly, the opening threshold pressure of the passive valve and characteristics of the diaphragm and other features of the cutter (e.g., the masses of various components and other mechanical properties) may be selected to achieve a desired resonance frequency. Thus, the cutter of a vitreous cutting apparatus may cut at a resonant frequency of the actuator. Additionally, the vitreous cutting apparatus may be self-valving such that valves automatically open and close upon the application of pneumatic power, causing the actuation of a vitreous cutter. This self-valving actuator eliminates the need to actively control valves (either by mechanically toggling or through a valve controller) in a surgical appliance to generate timed pulses of air. Instead, an approximately constant pressure can be applied continuously to a vitreous cutting apparatus to actuate a cutter. The application of constant pressure through a tube to a vitreous cutting apparatus eliminates pulses of air which may cause the vibration of the vitreous cutting apparatus.

In another embodiment, a resonant and self-valving actuator operable to actuate a vitreous cutter may utilize multiple pressurized chambers. For example, a diaphragm may et No. 3213 Patent Application define two chambers separated from each other by the diaphragm. A dual action actuator may alternately input and exhaust pressurized air or other fluid into each chamber, causing the alternate translational movement of the diaphragm and an actuating member coupled to the diaphragm. The alternate translational movement of the actuating member can be utilized to actuate a tube in a vitreous cutter.

Figure 5A:
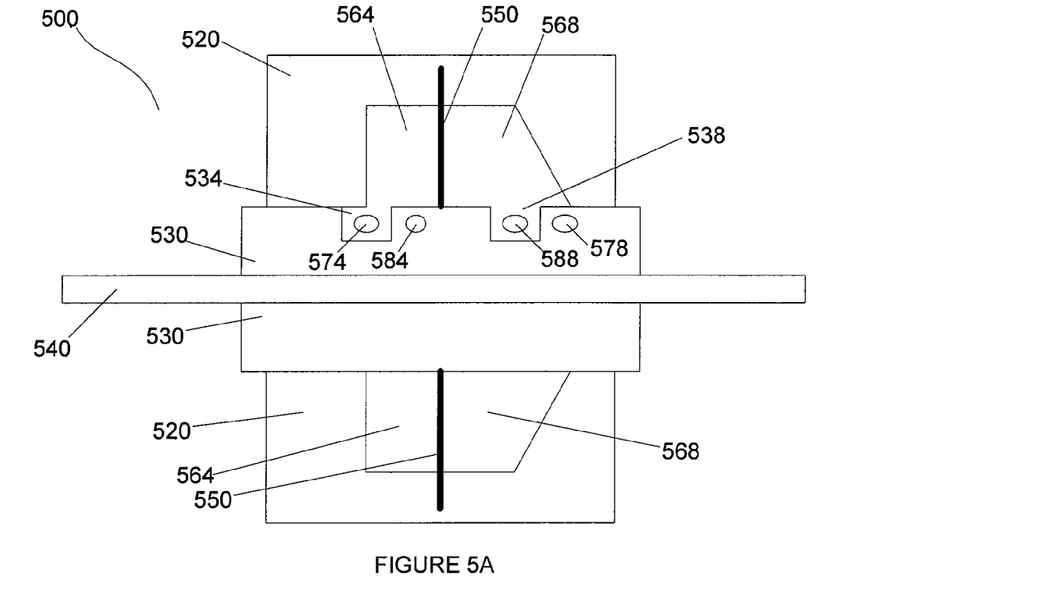
FIGS. 5A-5C are diagrammatic representations of a portion of another embodiment of a vitreous cutter.
Figure 5B:
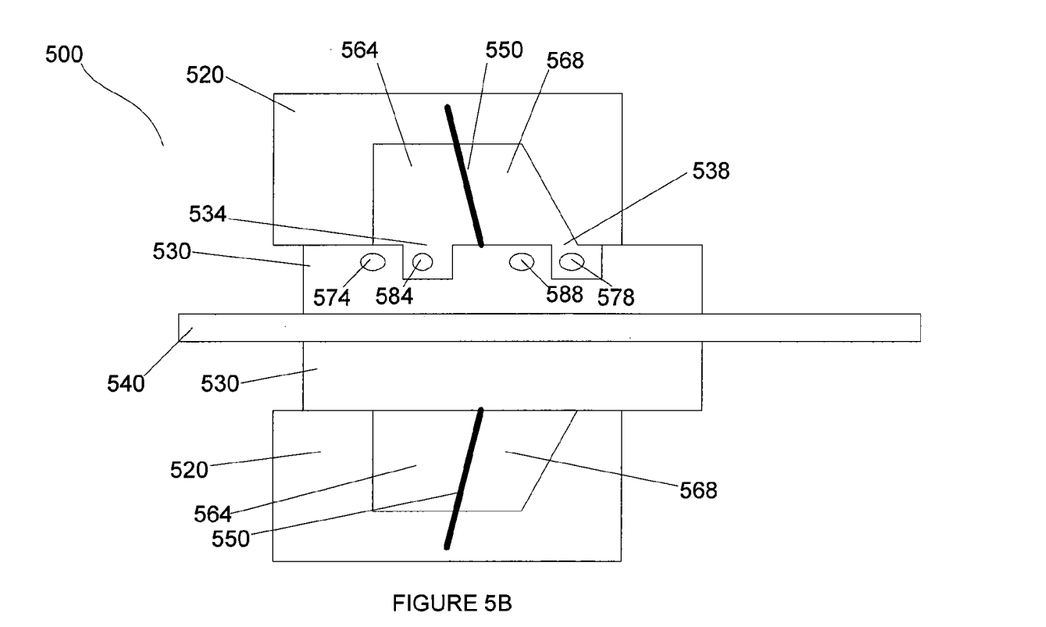
Figure 5C:
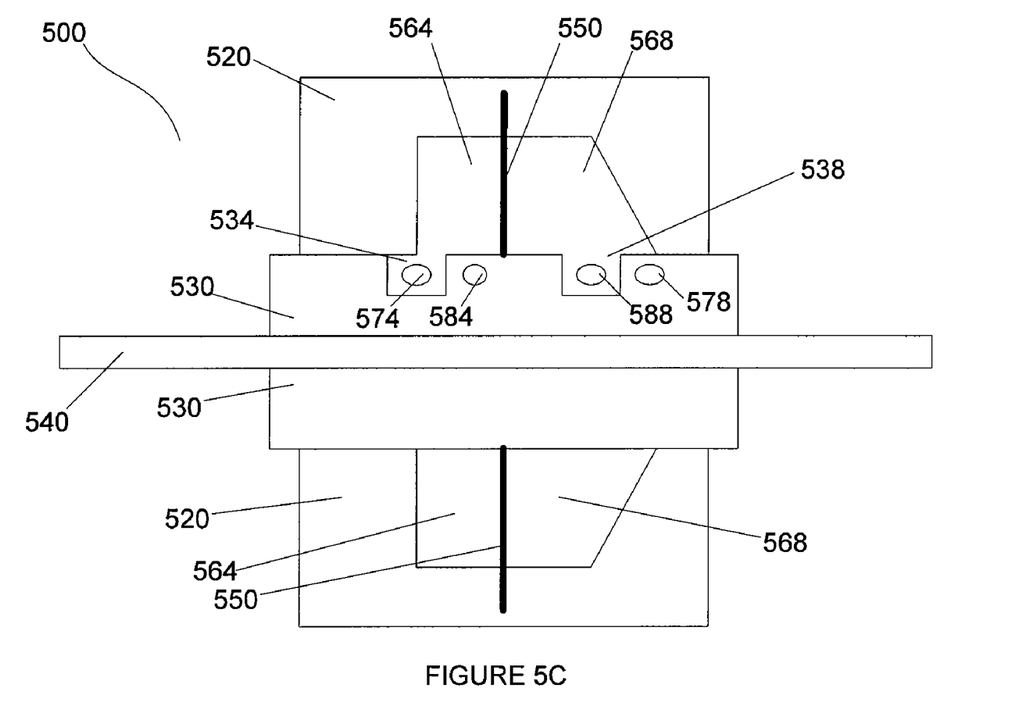

FIGS. 5A-5C are diagrammatic representations of a portion of a vitreous cutter 500. Vitreous cutter 500 can comprise a body 520, an actuating member 530 movable in body 520 and a diaphragm 550 coupled to body 520 and actuating member 530. Body 520, actuating member 530 and diaphragm 550 define chambers 564 and 568. Actuating member 530 is coupled to inner tube 540 such that lateral movement of actuating member 530 causes lateral movement of inner tube 540. Although shown as single pieces, each of actuating body 520, actuating member 530 and diaphragm 550 can comprise multiple pieces.

According to one embodiment, actuating member 530 can define gaps 534 and 538. For example, if actuating member 530 is disc shaped, actuating member 530 can include annular grooves. Body 520 can define input port 574 and exhaust port 584 to chamber 564 that are alternatively aligned with gap 534 and hence may be open to chamber 564. Body 520 can further define exhaust port 588 and input port 578 that are alternatively aligned with gap 538 and hence may be open to chamber 568. Actuating member 530 may initially be positioned such that input port 574 is coupled to gap 534 and gap 534 is coupled to chamber 564 such that input port 574 is coupled to chamber 564. Thus, if pressurized air or other fluid traverses input port 574, it enters chamber 564. Subsequently, if actuating member 530 moves forward in a translational movement such that input port 574 is no longer coupled to gap 534 but is instead isolated from chamber 564 by a portion of actuating member 530 and exhaust port 584 is coupled to gap 534 and to chamber 564 through the fluid coupling of gap 534 with chamber 564, pressurized air or other fluid may evacuate chamber 564 through exhaust port 584. Thus, the combination of input port 574 and exhaust port 584 operating in conjunction with actuating member 530 forms a spindle valve that can allow for pressurized air or other gas to enter and evacuate chamber 564.

Actuating member 530 may initially be positioned such that exhaust port 588 is coupled to gap 538 and gap 538 is coupled to chamber 568 such that exhaust port 588 is coupled to chamber 568. Thus, if pressurized air or other fluid is contained in chamber 568, it may evacuate out exhaust port 588 such that chamber 568 is unpressurized. Subsequently, if actuating member 530 moves forward in a translational movement such that exhaust port 588 is no longer coupled to gap 538 but is instead isolated from chamber 568 by a portion of actuating member 530 and input port 578 is coupled to gap 538 and to chamber 568 through the fluid coupling of gap 538 with chamber 568, pressurized air or other fluid traversing input port 578 may enter chamber 568. Thus, the combination of input port 578 and exhaust port 588 operating in conjunction with actuating member 530 forms a spindle valve that can allow for pressurized air or other gas to enter and evacuate chamber 568.

In FIG. 5A, a first pneumatic power source may be coupled to input port 574 upstream of input port 574. A second pneumatic power source may be coupled to input port 578 upstream of input port 578. Actuating member 530 may be positioned such that input port 574 is coupled to gap 534 and gap 534 is coupled to chamber 564, coupling input port 574 to chamber 564 such that pressurized air or other fluid traversing input port 574 enters chamber 564. As shown in FIG. 5A, actuating member 530 may further be positioned such that exhaust port 588 is coupled to gap 538 and gap 538 is coupled to chamber 568, coupling exhaust port 588 to chamber 568. Because exhaust port 588 may be coupled to atmosphere or a low pressure exhaust area, chamber 568 may be unpressurized such that chamber 568 is at atmosphere (or at least below the pressure entering chamber 564). The first pneumatic power source may be operated (e.g. by a doctor wishing to actuate a vitreous cutter) such that pneumatic power, in the form of pressurized air, gas, or other fluid traverses input port 574, entering chamber 564 with a velocity through input port 574. The pressurized air or other fluid fills chamber 564, causing the displacement of diaphragm 550 into unpressurized chamber 568, which in turn causes the translational movement of actuating member 530 and inner tube 540.

As shown in FIG. 5B, the pressurized air or other fluid which entered chamber 564 has displaced diaphragm 550 into chamber 568, causing translational movement of actuating member 530 and inner tube 540. The translational movement of actuating member 530 has caused a portion of actuating member 530 of block input port 574 such that pressurized air or other fluid is prevented from entering chamber 564 through input port 574. The translational movement of actuating member 530 has displaced the portion of actuating member 530 previously blocking exhaust port 584 such that exhaust port 584 is coupled to chamber 564 by gap 534. Exhaust port 584 may be at a lower pressure than chamber 564 or may vent to a lower pressure area relative to chamber 564, thus the pressurized air or other fluid vents out exhaust port 584. In one embodiment, exhaust port 584 vents to atmosphere such that the pressure in chamber 564 returns to atmosphere when exhaust port 584 is open to chamber 564.

As further shown in FIG. 5B, the displacement of diaphragm 550 into chamber 568 has caused translational movement of actuating member 530 and inner tube 540 such that exhaust port 588 is no longer coupled to gap 538 or chamber 568 but is instead blocked by a portion of actuating member 530 such that exhaust port 588 is isolated from chamber 568. In addition, the portion of actuating member 530 that previously blocked input port 578 has been displaced, and input port 578 is now coupled to gap 538 and gap 538 is coupled to chamber 568, coupling input port 578 to chamber 568. Because input port 578 is coupled to the second pneumatic power source, pneumatic power in the in the form of pressurized air or other fluid may traverse input port 578 to enter chamber 568 with a velocity through input port 578. The pressurized air or other fluid fills chamber 568, causing the displacement of diaphragm 550, which in turn causes the translational movement of actuating member 530 and inner tube 540.

The translational movement of actuating member 530 resulting from the displacement of diaphragm 550 due to pressurized air or other fluid entering chamber 568 may cause actuating member 530 to return to approximately is position as depicted in FIG. 5A. FIG. 5C depicts a time when pneumatic power entering chamber 568 through input port 578 has displaced diaphragm 550 such that actuating member 530 has returned to approximately its original position as depicted in FIG. 5A. As can be seen from FIG. 5C, chamber 564 is once again coupled to input port 574 and chamber 568 is coupled to exhaust port 588, causing the repetition of the processes described above with regard to FIGS. 5A-5C.

While depicted as holes in FIGS. 5A-5C, ports 574, 578, 584 and 588 are openings or passages traversing body 520. Various couplings may be used to couple ports 574 and 578 to one or more pneumatic power sources and various couplings may be used to couple ports 584 and 588 to atmosphere or other low pressure region. In one embodiment, the pneumatic power applied to ports 574 and 578 may be different, ensuring the back and forth translational movement of actuating member 530. In another embodiment, the pneumatic power applied to ports 574 or 578 may vary sinusoidally or otherwise over time, ensuring the translational movement of actuating member 530.

Diaphragm 550 may be a resilient diaphragm with a spring constant, e.g. a diaphragm of elastic polymer such as Mylar. The actuator may actuate at a resonant frequency based on the spring constant or other parameters of the diaphragm. The resonant frequency of actuation may further depend on the pneumatic power applied to the actuator.

Figure 6:
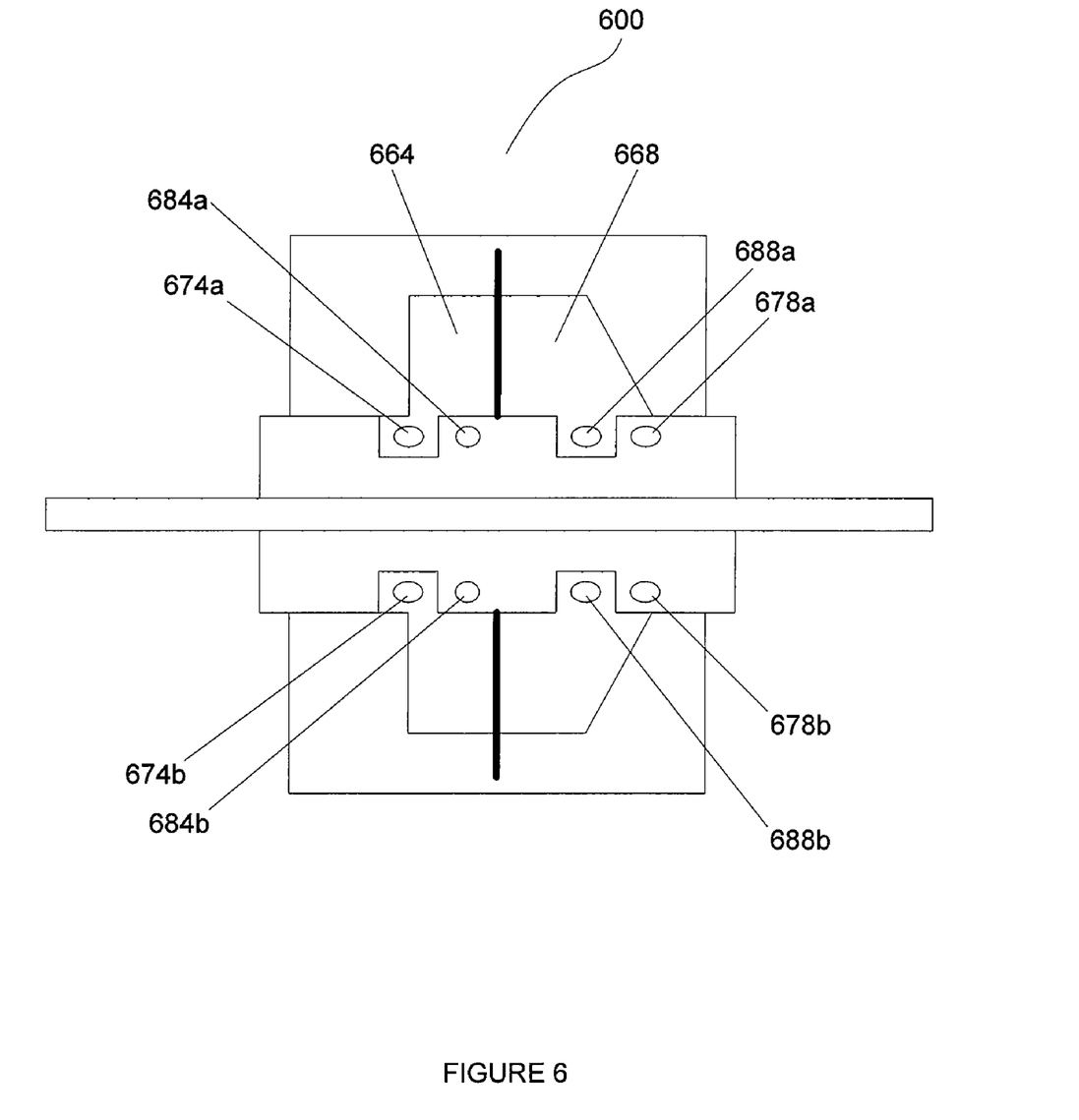
FIG. 6 is a diagrammatic representation of a portion of another embodiment a vitreous cutter.

In a further embodiment, a chamber of an actuator may be accessed by a plurality of ports. For example, an actuator may comprise multiple slide valves operable to input and exhaust pneumatic power from a chamber. Multiple input ports may ensure that pressurized air or other fluid fills a chamber approximately evenly. FIG. 6 is a diagrammatic representation of a portion of a vitreous cutter with chambers accessed by a plurality of ports. Chamber 664 may be accessed by input ports 674a and 674b, both of which are coupled to the same pneumatic power source. Chamber 664 may also be accessed by exhaust ports 684a and 684b, both of which may exhaust to atmosphere. Similarly, chamber 668 may be accessed by input ports 678a and 678b, both of which are coupled to the same pneumatic power source. Chamber 668 may also be accessed by exhaust ports 688a and 688b, both of which may exhaust to atmosphere. The embodiment of FIG. 6 can function similarly to that of FIGS. 5A-5C, but with pressurized fluid entering and exiting the chambers on either side of the diaphragm through multiple ports.

Embodiments of the above-described systems and methods may actuate a cutter at a high frequency to cause the cutter to cut a high number of cuts per minute relative to other actuators or cutters. The high number of cuts per minute allows fast cutting and non-pulsatile cutting. In addition, fast cutting may reduce the increments in which collagen fibers in vitreous are cut (e.g. to below ⅛ inch), reducing possible tension on the retina during vitreous surgery. In addition, actuating a cutter at a high frequency may ensure port-based flow limiting such that the rapid cutting action caused by the high frequency of actuation may serve to limit the amount of vitreous or other tissue affected by the suction and cutting action at any one time.

Although the systems and methods described herein have been described in detail herein with reference to the illustrated embodiments, it should be understood that the description is by way of example only and is not to be construed in a limiting sense. It is to be further understood, therefore, that numerous changes in the details of the described embodiment will be apparent, and may be made by, persons of ordinary skill in the art having reference to this description. It is contemplated that all such changes and additional embodiments are within scope of the invention as claimed below.

What is claimed is:

1. An apparatus, comprising:
an actuator body defining an input port and an exhaust port;
an actuating member movable in the actuator body from a first position to a second position, wherein the actuating member comprises a gap;
a diaphragm coupled to the actuator body and the actuating member, wherein the diaphragm, the actuator body and the actuating member together enclose a chamber accessed by the input port and the exhaust port, wherein a shape of the enclosed chamber changes with motion of the diaphragm;
a tube coupled to the actuating member;
wherein the actuating member is movable from the first position in which the gap of the actuating member at least partially overlaps the input port such that the input port is open to the chamber and the exhaust port is blocked by the actuating member and the second position in which the gap of the actuating member at least partially overlaps the exhaust port such that the exhaust port is open to the chamber and the input port is blocked by the actuating member.

2. The apparatus of claim 1, wherein the tube is an inner tube of a vitreous cutter.

3. The apparatus of claim 1, wherein the exhaust port exhausts to atmosphere.

4. The apparatus of claim 1, wherein the diaphragm is directly attached to the actuating member.

5. The apparatus of claim 1, wherein the diaphragm is directly attached to the actuator body.

6. The apparatus of claim 1, wherein the chamber is on only one side of the diaphragm.

7. The apparatus of claim 1, wherein diaphragm, the actuator body and the actuating member together enclose a chamber accessed by the input port and the exhaust port, wherein a shape of the enclosed chamber changes with motion of the diaphragm.

8. The apparatus of claim 7, wherein the actuating member is a single piece and wherein the diaphragm is directly attached to the actuating member and the actuator body.

9. An apparatus, comprising:
an actuator body defining a first input port, a second input port, a first exhaust port and a second exhaust port;
an actuating member movable in the actuator body from a first position to a second position;
a diaphragm coupled to the actuator body and the actuating member to form a first chamber accessed by the first input port and the first exhaust port and a second chamber on an obverse side of the diaphragm accessed by the second input port and the second exhaust port; and
a tube coupled to the actuating member;
wherein the actuating member comprises a first gap on a first chamber side of the diaphragm and a second gap on a second chamber side of the diaphragm;
wherein the actuating member is movable from:
the first position in which the first gap of the actuating member couples the first input port to the first chamber, the first exhaust port is isolated from the first chamber by the actuating member, to impede air flow through the first exhaust port, the second gap of the actuating member couples the second exhaust port to the second chamber and the second input port is isolated from the second chamber by the actuating member, to impede air flow through the second input port,
to the second position in which the first gap of the actuating member couples the first exhaust port to the first chamber and the first input port is isolated from the first chamber by the actuating member, to impede air flow through the first input port, the second gap of the actuating member couples the second input port to the second chamber and the second exhaust port is isolated from the second chamber by the actuating member, to impede air flow through the first input port.

10. The apparatus of claim 9, wherein actuating member moves back and forth from the first position to the second position at a frequency based on pneumatic power applied to the first input port and the pneumatic power applied to the second input port.

11. The apparatus of claim 9, wherein the tube is an inner tube of a vitreous cutter.

12. The apparatus of claim 9, wherein the first exhaust port and the second exhaust port exhaust to atmosphere.

13. The apparatus of claim 9, wherein the tube is directly attached to the actuating member.

14. The apparatus of claim 9, wherein the diaphragm is directly attached to the actuator body and the actuating member.

15. An apparatus, comprising:
an actuator body defining an input port and an exhaust port;
an actuating member movable in the actuator body from a first position to a second position, wherein the actuating member comprises a gap;
a diaphragm coupled to the actuator body and the actuating member to form a chamber accessed by the input port and the exhaust port;
a tube coupled to the actuating member; and
a passive valve located upstream of the input port having a threshold opening pressure;
wherein the actuating member is movable from the first position in which the gap of the actuating member at least partially overlaps the input port such that the input port is open to the chamber and the exhaust port is blocked by the actuating member and the second position in which the gap of the actuating member at least partially overlaps the exhaust port such that the exhaust port is open to the chamber and the input port blocked by the actuating member.

16. The apparatus of claim 15, wherein the passive valve is a pop-off valve.

17. The apparatus of claim 15, wherein the passive valve is a reed valve.

18. The apparatus of claim 15, further comprising a pneumatic pressure source to provide pressurized air to the passive valve at a first pressure and a second pressure, wherein the first pressure is below the opening threshold pressure of the passive valve and the second pressure is above the opening threshold pressure of the passive valve.

19. The apparatus of claim 18, wherein the second pressure and mechanical characteristics of the diaphragm are selected to cause the actuating member to actuate with a selected frequency.

* * * * *